(12) United States Patent
Bryant et al.

(10) Patent No.: US 11,763,926 B2
(45) Date of Patent: *Sep. 19, 2023

(54) SYSTEM AND METHOD FOR ADMINISTERING AN INFUSIBLE FLUID

(71) Applicant: DEKA Products Limited Partnership, Manchester, NH (US)

(72) Inventors: Robert J. Bryant, Manchester, NH (US); Marc A. Mandro, Bow, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/556,399

(22) Filed: Aug. 30, 2019

(65) Prior Publication Data
US 2019/0381241 A1    Dec. 19, 2019

Related U.S. Application Data

(63) Continuation of application No. 14/935,874, filed on Nov. 9, 2015, now Pat. No. 10,398,835, which is a continuation of application No. 12/249,636, filed on Oct. 10, 2008, now Pat. No. 9,180,245.

(51) Int. Cl.
| | |
|---|---|
| *A61M 5/14* | (2006.01) |
| *G16H 20/17* | (2018.01) |
| *A61M 5/145* | (2006.01) |
| *A61M 5/168* | (2006.01) |
| *A61M 5/142* | (2006.01) |

(52) U.S. Cl.
CPC .......... *G16H 20/17* (2018.01); *A61M 5/1452* (2013.01); *A61M 5/168* (2013.01); *A61M 2005/14208* (2013.01); *A61M 2230/201* (2013.01)

(58) Field of Classification Search
CPC ...... A61M 2005/14208; A61M 5/1723; A61M 2005/14296; A61M 2205/52; A61M 2005/1405; A61M 2205/50; A61M 5/16827; G06F 19/3456; G06F 19/3468; G06F 19/3406
See application file for complete search history.

(56) References Cited

U.S. PATENT DOCUMENTS

| | | | |
|---|---|---|---|
| 4,146,029 A | * | 3/1979 | Ellinwood, Jr. ... A61N 1/37211 604/891.1 |
| 4,468,439 A | | 8/1984 | Ohara et al. |
| 4,601,707 A | * | 7/1986 | Albisser ................ A61M 5/148 604/151 |

(Continued)

FOREIGN PATENT DOCUMENTS

WO    WO-03008014 A2 *  1/2003  ........ A61M 5/14244

*Primary Examiner* — William R Carpenter
(74) *Attorney, Agent, or Firm* — McCormick, Paulding & Huber PLLC

(57) ABSTRACT

A method, computer program product, and infusion pump assembly for administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

10 Claims, 4 Drawing Sheets

(56) References Cited

U.S. PATENT DOCUMENTS

| | | | | |
|---|---|---|---|---|
| 4,696,671 | A | * | 9/1987 | Epstein ............. A61M 5/14224 |
| | | | | 128/DIG. 13 |
| 5,236,416 | A | | 8/1993 | McDaniel et al. |
| 5,378,231 | A | * | 1/1995 | Johnson ............ A61M 5/16827 |
| | | | | 128/DIG. 13 |
| 5,405,614 | A | * | 4/1995 | D'Angelo ............ A61K 9/7023 |
| | | | | 604/20 |
| 6,336,913 | B1 | | 1/2002 | Spohn et al. |
| 7,406,683 | B2 | | 7/2008 | Kalidindi |
| 10,207,048 | B2 | | 2/2019 | Gray et al. |
| 2007/0112298 | A1 | * | 5/2007 | Mueller ............ A61M 5/14244 |
| | | | | 600/316 |
| 2011/0271247 | A1 | | 11/2011 | Hedley et al. |

\* cited by examiner

18

SYSTEM AND METHOD FOR ADMINISTERING AN INFUSIBLE FLUID

CROSS REFERENCE TO RELATED APPLICATIONS

This application is a continuation of U.S. patent application Ser. No. 14/935,874 filed on Nov. 9, 2015, which is a continuation of U.S. patent application Ser. No. 12/249,636 filed on Oct. 10, 2008, each of which is hereby incorporated by reference herein in its entirety.

TECHNICAL FIELD

This disclosure relates to infusion pump assemblies and, more particularly, to infusion pump assemblies configured to administer sequential, multi-part, infusion events and one-time infusion events.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

SUMMARY OF DISCLOSURE

In a first implementation, a method includes administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

In another implementation, a computer program product resides on a computer readable medium that has a plurality of instructions stored on it. When executed by a processor, the instructions cause the processor to perform operations including administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

In another implementation, an infusion pump assembly is configured to perform operations including administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
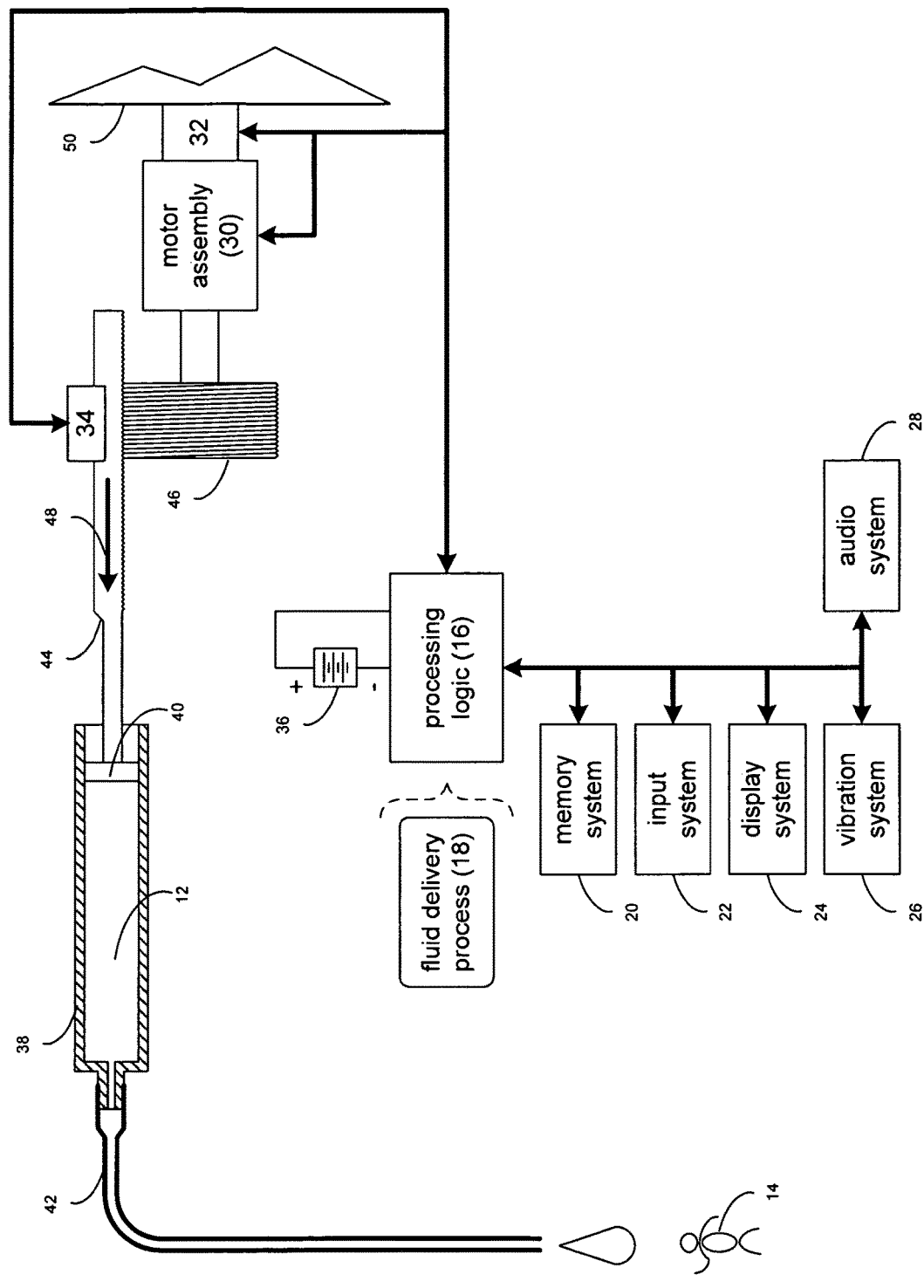
FIG. 1 is a diagrammatic view of an infusion pump assembly executing a fluid delivery process.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs Infusion pump assembly 10 may include processing logic 16 that executes one or more processes that may be required for infusion pump assembly 10 to operate properly. Processing logic 16 may include one or more microprocessors (not shown), one or more input/output controllers (not shown), and cache memory devices (not shown). One or more data buses and/or memory buses may be used to interconnect processing logic 16 with one or more subsystems.

Processing logic 16 may execute fluid delivery process 18 that (as will be discussed below in greater detail) may delay the administration of at least a portion of a sequential, multi-part, infusion event until a one-time infusion event is completely administered.

Examples of the subsystems interconnected with processing logic 16 may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a primary battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

The instruction sets and subroutines of fluid delivery process 18, which may be stored on a storage device (e.g., memory system 20) accessible by processing logic 16, may be executed by one or more processors (not shown) and one or more memory architectures (e.g., memory system 20) included within infusion pump assembly 10. Examples of memory system 20 may include but are not limited to: a random access memory; a read-only memory; and a flash memory.

Infusion pump assembly 10 may include reservoir assembly 38 configured to contain infusible fluid 12. In some embodiments, the reservoir assembly 38 may be a reservoir assembly similar to that described in U.S. Patent Application No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may form a pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the appropriate drive signals to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 42, thus increasing the torque and resolution of motor assembly 30 by a factor of three-thousand.

As discussed above, infusion pump assembly 10 may be configured to deliver infusible fluid 12 to user 14. Infusible fluid 12 may be delivered to user 14 via one or more different infusion event types. For example, infusion pump assembly 10 may deliver infusible fluid 12 via may a sequential, multi-part, infusion event (that may include a plurality of discrete infusion events) and/or a one-time infusion event.

Examples of such a sequential, multi-part, infusion event may include but are not limited to a basal infusion event and an extended-bolus infusion event. As is known in the art, a basal infusion event refers to the repeated injection of small (e.g. 0.05 unit) quantities of infusible fluid 12 at a predefined interval (e.g. every three minutes) that may be repeated indefinitely. Further, the basal infusion rates may be pre-programmed and may include specified rates for pre-programmed time-frames, e.g., a rate of 0.50 units per hour from 6 am-3 pm; a rate of 0.40 units per hour from 3 pm-10 pm; and a rate of 0.35 units per hour from 10 pm-6 am. However, similarly, the basal rate may be 0.025 units per hour, and may not change according to pre-programmed time-frames. The basal rates may be repeated regularly/daily until otherwise changed.

Further and as is known in the art, an extended-bolus infusion event may refer to the repeated injection of small (e.g. 0.05 unit) quantities of infusible fluid 12 at a predefined interval (e.g. every three minutes) that is repeated for a defined number of intervals (e.g., three intervals) or for a defined period of time (e.g., nine minutes). An extended-bolus infusion event may occur simultaneously with a basal infusion event.

Figure 2:
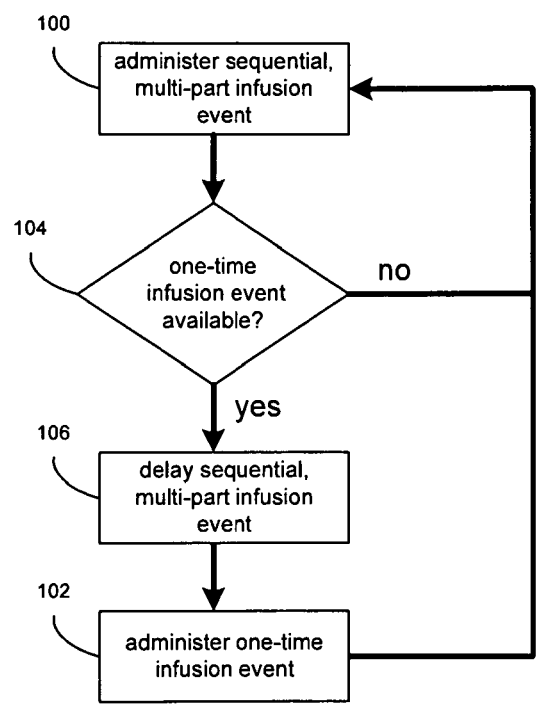
FIG. 2 is a flowchart of the fluid delivery process of FIG. 1.
Figure 3:
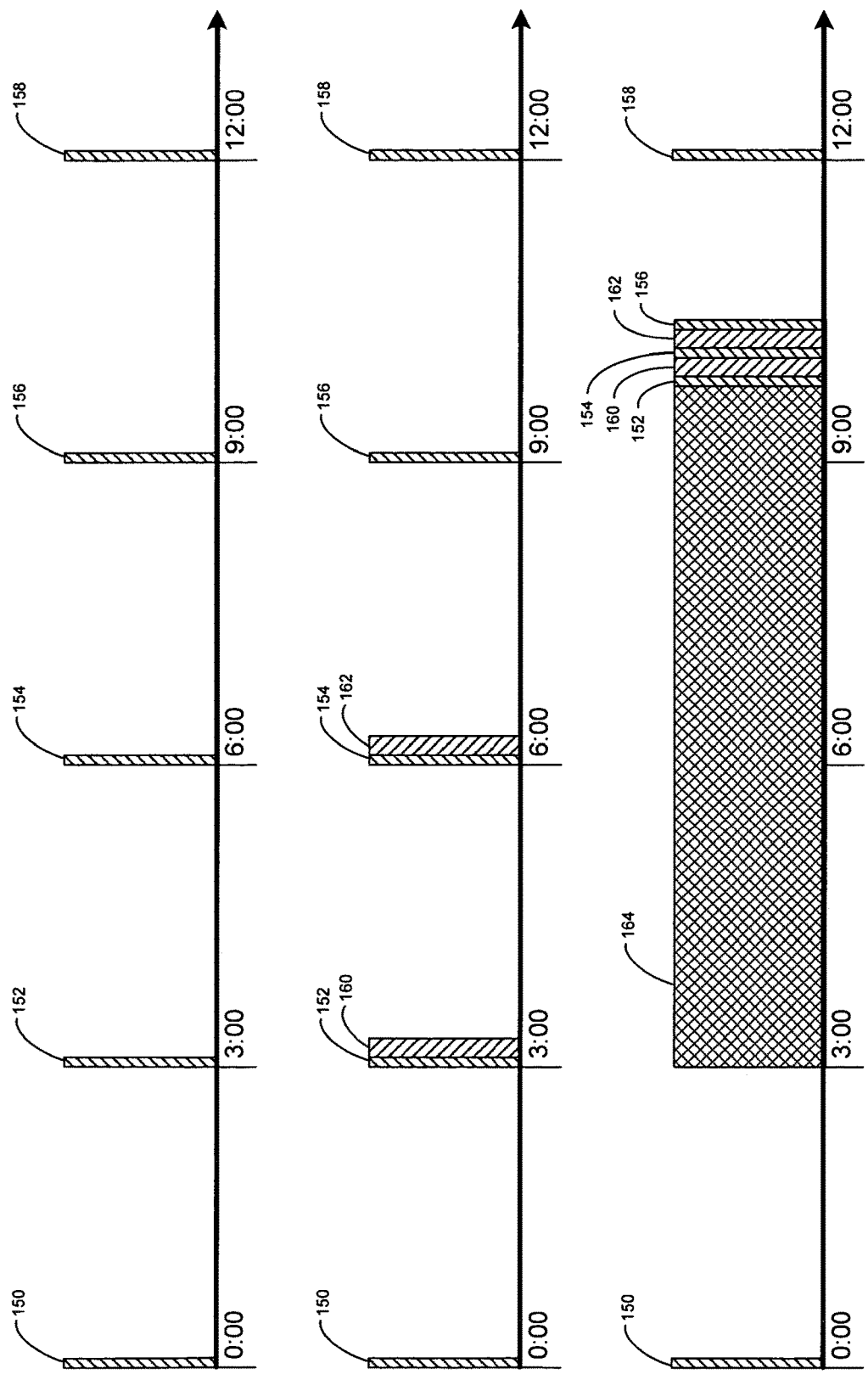
FIG. 3 is a timeline illustrative of a plurality of discrete infusion events.

Referring also to FIGS. 2-3, assume for illustrative purposes only that user 14 configures infusion pump assembly 10 to administer a basal dose (e.g. 0.05 units) of infusible fluid 12 every three minutes. As discussed above, infusion pump assembly 10 may include input system 22 and display system 24.

Accordingly, user 14 may utilize input system 22 to define a basal infusion event for infusible fluid 12 (e.g., 1.00 units per hour), which may be confirmed via display system 24. While, in this example, the basal infusion event is described as 1.00 units per hour, this is for illustrative purposes only and is not intended to be a limitation of this disclosure, as either or both of the unit quantity and time period may be adjusted upward or downward. Infusion pump assembly 10 may then determine an infusion schedule based upon the basal infusion event defined; and may administer 100 infusible fluid 12. For example, infusion pump assembly 10 may deliver 0.05 units of infusible fluid 12 every three minutes, resulting in the delivery of the basal dose of infusible fluid 12 defined by the user (i.e., 1.00 units per hour).

Once defined and/or confirmed, fluid delivery process 18 may administer 100 the sequential, multi-part, infusion event (e.g., 0.05 units of infusible fluid 12 every three minutes). Accordingly, while administering 100 the sequential, multi-part, infusion event, infusion pump assembly 10: may infuse a first 0.05 unit dose 150 of infusible fluid 12 at t=0:00 (i.e., a first discrete infusion event), may infuse a second 0.05 unit dose 152 of infusible fluid 12 at t=3:00 (i.e., a second discrete infusion event); may infuse a third 0.05 unit dose 154 of infusible fluid 12 at t=6:00 (i.e., a third discrete infusion event); may infuse a fourth 0.05 unit dose 156 of infusible fluid 12 at t=9:00 (i.e., a fourth discrete infusion event); and may infuse a fifth 0.05 unit dose 158 of infusible fluid 12 at t=12:00 (i.e., a fifth discrete infusion event). As discussed above, this pattern of infusing 0.05 unit doses of infusible fluid 12 every three minutes may be repeated indefinitely in this example, as this is an illustrative example of a basal infusion event.

Further, assume for illustrative purposes that infusible fluid 12 is insulin and sometime after the first 0.05 unit dose 150 of infusible fluid 12 is administered 100 by fluid delivery process 18 (but before the second 0.05 unit dose 150 of infusible fluid 12 is administered 100 by fluid delivery process 18), user 14 checks their blood glucose level and realizes that their blood glucose level is running a little higher than normal. Accordingly, user 14 may define an extended bolus infusion event via fluid delivery process 18.

An extended bolus infusion event may refer to the continuous infusion of a defined quantity of infusible fluid 12 over a finite period of time. However, as such an infusion methodology is impractical/undesirable for an infusion pump assembly, when administered by such an infusion pump assembly, an extended bolus infusion event may refer to the infusion of additional small doses of infusible fluid 12 over a finite period of time.

Accordingly, user 14 may utilize input system 22 to define an extended bolus infusion event for infusible fluid 12 (e.g., 0.20 units over the next six minutes), which may be confirmed via display system 24. While, in this example, the extended bolus infusion event is described as 0.20 units over the next six minutes, this is for illustrative purposes only and is not intended to be a limitation of this disclosure, as either or both of the unit quantity and total time interval may be adjusted upward or downward. Once defined and/or confirmed, fluid delivery process 18 may determine an infusion schedule based upon the extended bolus infusion event defined; and may administer 100 infusible fluid 12. For example, infusion pump assembly 10 may deliver 0.10 units of infusible fluid 12 every three minutes for the next two interval cycles (or six minutes), resulting in the delivery of the extended bolus dose of infusible fluid 12 defined by the user (i.e., 0.20 units over the next six minutes).

Accordingly, while administering 100 the second, sequential, multi-part, infusion event, infusion pump assembly 10 may infuse a first 0.10 unit dose 160 of infusible fluid 12 at t=3:00 (e.g., after administering the second 0.05 unit dose 152 of infusible fluid 12). Infusion pump assembly 10 may also infuse a second 0.10 unit dose 162 of infusible fluid 12 at t=6:00 (e.g., after administering the third 0.05 unit dose 154 of infusible fluid 12).

Assume for illustrative purposes only that after user 14 programs infusion pump assembly 10 to administer 100 the first sequential, multi-part, infusion event (i.e., 0.05 units infused every three minute interval repeated continuously) and administer 100 the second sequential, multi-part, infusion event (i.e., 0.10 units infused every three minute interval for two intervals), user 14 decides to eat a very large meal. Predicting that their blood glucose level might increase considerably, user 14 may program infusion pump assembly 10 (via input system 22 and/or display system 24) to administer 102 a one-time infusion event. An example of such a one-time infusion event may include but is not limited to a normal bolus infusion event. As is known in the art, a normal bolus infusion event refers to a one-time infusion of infusible fluid 12.

For illustrative purposes only, assume that user 14 wishes to have infusion pump assembly 10 administer 102 a bolus dose of thirty-six units of infusible fluid 12. Fluid delivery process 18 may monitor the various infusion events being administered by fluid delivery process 18 to determine 104 whether a one-time infusion event is available to be administered. If 104 a one-time infusion event is available for administration 102, fluid delivery process 10 may delay 106 the administration of at least a portion of the sequential, multi-part, infusion event.

Continuing with the above-stated example, once user 14 completes the programming of fluid delivery process 18 to deliver one-time infusion event 164 (i.e., the thirty-six unit bolus dose of infusible fluid 12), upon fluid delivery process 18 determining 104 that the one-time infusion event is available for administration 102, fluid delivery process 18 may delay 106 the administration 100 of each sequential, multi-part infusion event and administer 102 the available one-time infusion event.

Specifically and as discussed above, prior to user 14 programming fluid delivery process 18 to deliver one-time infusion event 164, infusion delivery process 18 was administering 100 a first sequential, multi-part, infusion event (i.e., 0.05 units infused every three minute interval repeated continuously) and administering 100 a second sequential, multi-part, infusion event (i.e., 0.10 units infused every three minute interval for two intervals).

For illustrative purposes only, the first sequential, multi-part, infusion event may be represented within FIG. 3 as 0.05 unit dose 150 @ t=0:00, 0.05 unit dose 152 @ t=3:00, 0.05 unit dose 154 @ t=6:00, 0.05 unit dose 156 @ t=9:00, and 0.05 unit dose 158 @ t=12:00. As the first sequential, multi-part, infusion event as described above is a basal infusion event, infusion pump assembly 10 (in conjunction with fluid delivery process 18) may continue to infuse 0.05 unit doses of infusible fluid 12 at three minute intervals indefinitely (i.e., until the procedure is cancelled by user 14).

Further and for illustrative purposes only, the second sequential, multi-part, infusion event may be represented within FIG. 3 as 0.10 unit dose 160 @ t=3:00 and 0.10 unit dose 162 @ t=6:00. As the second sequential, multi-part, infusion event is described above as an extended bolus infusion event, infusion pump assembly 10 (in conjunction with fluid delivery process 18) may continue to infuse 0.10 unit doses of infusible fluid 12 at three minute intervals for exactly two intervals (i.e., the number of intervals defined by user 14).

Continuing with the above-stated example, upon fluid delivery process 18 determining 104 that the thirty-six unit normal bolus dose of infusible fluid 12 (i.e., one-time infusion event 164) is available for administration 102, fluid delivery process 18 may delay 106 the administration 100 of each sequential, multi-part infusion event and may start administering 102 one-time infusion event 164 that is available for administration.

Accordingly and for illustrative purposes only, assume that upon completion of the programming of infusion pump assembly 10 to deliver the thirty-six unit normal bolus does of infusible fluid 12 (i.e., the one-time infusion event), fluid delivery process begins administering 102 one-time infusion event 164. Being that one-time infusion event 164 is comparatively large, it may take longer than three minutes (i.e., the time interval between individual infused doses of the sequential, multi-part, infusion events), one or more of the individual infused doses of the sequential, multi-part, infusion events may need to be delayed.

Specifically, assume that it will take infusion pump assembly 10 greater than six minutes to infuse thirty-six units of infusible fluid 12. Accordingly, fluid delivery process 18 may delay 0.05 unit dose 152 (i.e., scheduled to be infused @ t=3:00), 0.05 unit dose 154 (i.e., scheduled to be infused @ t=6:00), and 0.05 unit dose 156 (i.e., scheduled to be infused @ t=9:00) until after one-time infusion event 164 (i.e., the thirty-six unit normal bolus dose of infusible fluid 12) is completely administered. Further, fluid delivery process 18 may delay 0.10 unit dose 160 (i.e., scheduled to be infused @ t=3:00 and 0.10 unit dose 162 (i.e., scheduled to be infused @ t=6:00) until after one-time infusion event 164.

Once administration 102 of one-time infusion event 164 is completed by fluid delivery process 18, any discrete infusion events included within the sequential, multi-part, infusion event that were delayed may be administered 100 by fluid delivery process 18.

Accordingly, once one-time infusion event 164 (i.e., the thirty-six unit normal bolus dose of infusible fluid 12) is completely administered 102, fluid delivery process 18 may administer 100 0.05 unit dose 152, 0.05 unit dose 154, 0.05 unit dose 156, 0.10 unit dose 160, and 0.10 unit dose 162.

While fluid delivery process 18 is shown to administer 100 0.05 unit dose 152, then 0.10 unit dose 160, then 0.05 unit dose 154, then 0.10 unit dose 162, and then 0.05 unit dose 156, this is for illustrative purposes only and is not intended to be a limitation of this disclosure, as other configurations are possible and are considered to be within the scope of this disclosure. For example, upon fluid delivery process 18 completing the administration 102 of one-time infusion event 164 (i.e., the thirty-six unit normal bolus dose of infusible fluid 12), fluid delivery process 18 may administer 100 all of the delayed discrete infusion events associated with the first sequential, multi-part infusion event (i.e., namely 0.05 unit dose 152, 0.05 unit dose 154, and 0.05 unit dose 156. Fluid delivery process 18 may then administer 100 all of the delayed discrete infusion events associated with the second sequential, multi-part infusion event (i.e., 0.10 unit dose 160, and 0.10 unit dose 162).

While one-time infusion event 164 (i.e., the thirty-six unit normal bolus dose of infusible fluid 12) is shown as being infused beginning at t=3:00, this is for illustrative purposes only and is not intended to be a limitation of this disclosure. Specifically, fluid delivery process 18 may not need to begin infusing one-time infusion event 164 at one of the three-minute intervals (e.g., t=0:00, t=3:00, t=6:00, t=9:00, or t=12:00) and may begin administering 102 one-time infusion event 164 at any time.

While each discrete infusion event (e.g., 0.05 unit dose 152, 0.05 unit dose 154, 0.05 unit dose 156, 0.10 unit dose 160, and 0.10 unit dose 162) and one-time infusion event 164 are shown as being a single event, this is for illustrative purposes only and is not intended to be a limitation of this disclosure. Specifically, at least one of the plurality of discrete infusion events e.g., 0.05 unit dose 152, 0.05 unit dose 154, 0.05 unit dose 156, 0.10 unit dose 160, and 0.10 unit dose 162) may include a plurality of discrete infusion sub-events. Further, one-time infusion event 164 may include a plurality of one-time infusion sub-events.

Figure 4:
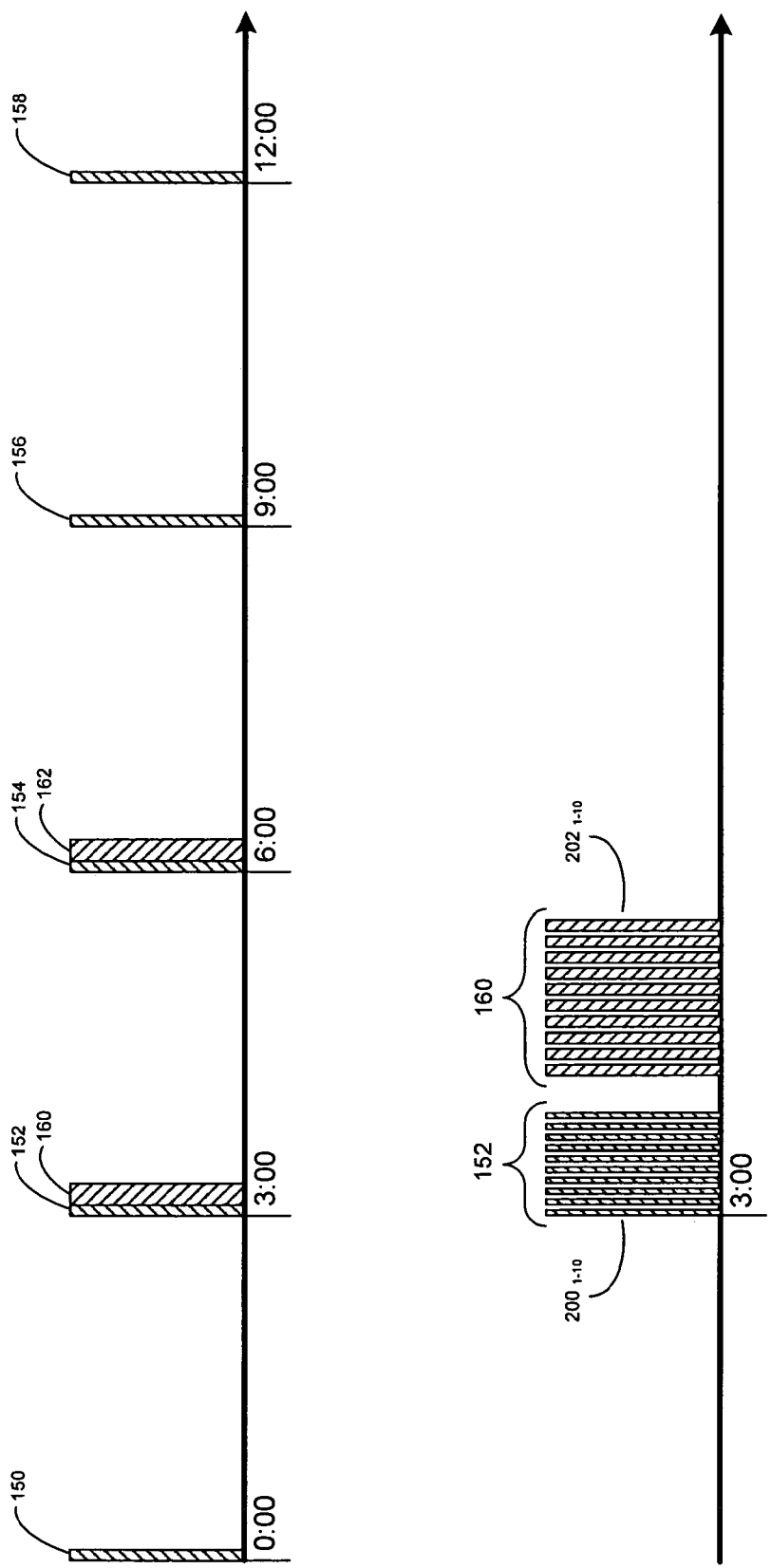
FIG. 4 is a more detailed view of two discrete infusion events included within FIG. 3.

Referring also to FIG. 4 and for illustrative purposes, 0.05 unit dose 152 is shown to include ten discrete infusion sub-events (e.g., infusion sub-events $200_{1-10}$), wherein a 0.005 unit dose of infusible fluid 12 is infused during each of the ten discrete infusion sub-events. Additionally, 0.10 unit dose 160 is shown to include ten discrete infusion sub-events (e.g., infusion sub-events $202_{1-10}$), wherein a 0.01 unit dose of infusible fluid 12 is delivered during each of the ten discrete infusion sub-events. Further, one-time infusion event 164 may include e.g., 360 one-time infusion sub-events (not shown), wherein a 0.1 unit dose of infusible fluid 12 is delivered during each of the 360 one-time infusion sub-events. The number of sub-events defined above and the quantity of infusible fluid 12 delivered during each sub-event is solely for illustrative purposes only and is not intended to be a limitation of this disclosure, as the number of sub-events and/or the quantity of infusible fluid 12 delivered during each sub-event may be increased or decreased depending upon e.g., the design criteria of infusion pump assembly 10 and/or the implementation of fluid delivery process 18.

Before, after, or in between the above-described infusion sub-events, infusion pump assembly 10 may confirm the proper operation of infusion pump assembly 10 through the use of e.g., force sensor 32 (i.e., which may determine the occurrence of an occlusion) and displacement detection device 34 (i.e., which may determine the occurrence of a mechanical failure).

A number of implementations have been described. Nevertheless, it will be understood that various modifications may be made. Accordingly, other implementations are within the scope of the following claims.

What is claimed is:

1. An infusion pump assembly comprising a processor including processing logic configured to perform operations comprising:
   administering a sequential, multi-part, basal infusion event with an infusible fluid, wherein the sequential, multi-part, basal infusion event includes a first plurality of discrete infusion events;
   administering a sequential, multi-part, extended bolus infusion event with the infusible fluid, wherein the sequential, multi-part, extended bolus infusion event includes a second plurality of discrete infusion events;
   determining through the processing logic whether a one-time infusion event is available to be administered; and
   if the one-time infusion event is available to be administered with the infusible fluid, delaying the administration of at least a portion of the first plurality of discrete infusion events included within the sequential, multi-part, basal infusion event and at least a portion of the second plurality of discrete infusion events within the sequential, multi-part, extended bolus infusion event; and
   administering the one-time infusion event.

2. The infusion pump assembly of claim 1, wherein the infusion pump assembly is further configured to perform operations comprising:
   once the administration of the one-time infusion event is completed, administering the at least a portion of the first plurality of discrete infusion events included within the sequential, multi-part, basal infusion event and the at least a portion of the second plurality of discrete infusion events within the sequential, multi-part, extended bolus infusion event.

3. The infusion pump assembly of claim 1 wherein the one-time infusion event includes a normal bolus infusion event.

4. The infusion pump assembly of claim 1 wherein at least one of the first plurality of discrete infusion events includes a plurality of discrete infusion sub-events.

5. The infusion pump assembly of claim 1 wherein the one-time infusion event includes a plurality of one-time infusion sub-events.

6. An infusion pump assembly comprising a processor including processing logic configured to perform operations comprising:
   administering a sequential, multi-part, basal infusion event with an infusible fluid;
   administering an extended bolus infusion event with the infusible fluid;
   determining through the processing logic whether a one-time infusion event is available to be administered; and
   if a one-time infusion event is available to be administered with the infusible fluid, delaying the administration of at least a portion of the sequential, multi-part, basal infusion event and at least a portion of the extended bolus infusion event; and
   administering the one-time infusion event.

7. The infusion pump assembly of claim 6 further comprising:
   administering the sequential, multi-part, basal infusion event after the one-time infusion event has completed; and
   administering the extended bolus infusion event after the one-time infusion event has completed.

8. The infusion pump assembly of claim 7 wherein the extended bolus infusion event occurs simultaneously with the sequential, multi-part, basal infusion event.

9. The infusion pump assembly of claim 6 wherein the one-time infusion event includes a normal bolus infusion event.

10. The infusion pump assembly of claim 6 wherein the one-time infusion event includes a plurality of one-time infusion sub-events.

* * * * *